US008632529B2

(12) United States Patent
Bencini

(10) Patent No.: US 8,632,529 B2
(45) Date of Patent: Jan. 21, 2014

(54) ABLATION DEVICES AND METHODS OF USE

(75) Inventor: Robert F. Bencini, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/549,840

(22) Filed: Jul. 16, 2012

(65) Prior Publication Data

US 2012/0283716 A1 Nov. 8, 2012

Related U.S. Application Data

(62) Division of application No. 12/351,072, filed on Jan. 9, 2009, now Pat. No. 8,235,977.

(60) Provisional application No. 61/020,510, filed on Jan. 11, 2008.

(51) Int. Cl.
*A61B 18/18* (2006.01)
(52) U.S. Cl.
USPC .......................................................... 606/21
(58) Field of Classification Search
USPC ................. 604/101.01, 101.05, 96.01; 606/191–195, 21; 607/113, 106; 128/898; 62/50.1, 51.2
See application file for complete search history.

(56) References Cited

U.S. PATENT DOCUMENTS

| 3,045,677 | A | * | 7/1962 | Wallace | 604/101.05 |
| 4,484,579 | A | * | 11/1984 | Meno et al. | 606/194 |
| 5,019,042 | A | * | 5/1991 | Sahota | 604/101.01 |
| 5,462,521 | A | | 10/1995 | Brucker et al. | |
| 5,807,395 | A | | 9/1998 | Mulier et al. | |
| 5,868,735 | A | | 2/1999 | Lafontaine et al. | |
| 6,132,397 | A | | 10/2000 | Davis et al. | |
| 6,468,297 | B1 | * | 10/2002 | Williams et al. | 607/113 |
| 6,517,533 | B1 | | 2/2003 | Swaminathan | |
| 6,537,271 | B1 | | 3/2003 | Murray et al. | |
| 6,575,966 | B2 | | 6/2003 | Lane et al. | |
| 6,602,242 | B1 | | 8/2003 | Fung | |
| 6,605,030 | B2 | * | 8/2003 | Weinberger | 600/3 |
| 6,796,979 | B2 | | 9/2004 | Lentz | |
| 6,811,550 | B2 | | 11/2004 | Holland et al. | |
| 8,235,977 | B2 | | 8/2012 | Bencini | |

FOREIGN PATENT DOCUMENTS

| WO | 9927862 A1 | 6/1999 |
| WO | 0164145 A1 | 9/2001 |
| WO | 02102234 A2 | 12/2002 |
| WO | 03039338 A2 | 5/2003 |

* cited by examiner

*Primary Examiner* — Manuel Mendez
(74) *Attorney, Agent, or Firm* — Seager, Tufte & Wickhem, LLC

(57) ABSTRACT

Described herein are various methods and devices for delivering cryoablative therapy. One such device includes a cryoablation chamber and a volume displacement chamber. In use, the volume displacement chamber can be expanded to occupy a non-therapeutic volume.

9 Claims, 4 Drawing Sheets

ABLATION DEVICES AND METHODS OF USE

This application is a divisional of U.S. application Ser. No. 12/351,072, filed Jan. 9, 2009 now U.S. Pat. No. 8,235,977, which claims priority to Provisional Application Ser. No. 61/020,510 entitled "Ablation Devices and Methods of Use" filed Jan. 11, 2008, which is incorporated herein by reference.

BACKGROUND

Atrial fibrillation is a common cardiac arrhythmia. Patient's suffering from atrial fibrillation experience malfunctions of their heart's electrical system that cause the atria to quiver rapidly instead of beating in a normal pattern. This quivering prevents the heart from properly pumping blood and can eventually lead to clot formation and stroke.

Treatments for atrial fibrillation include drug therapy, electrocardioversion, and surgical or intravascular ablation techniques. Surgical and catheter based techniques have grown in popularity because drug therapy may be ineffective in some patients, showing success rates as low as fifty percent. Along with this low success rate, drug therapies also have deleterious side effects.

Surgical ablation requires a more invasive procedure whereby the surgeon creates a maze-like pattern of incisions on the inside of the patient's atria. The scarring that results acts to block the abnormal electrical pathways in the heart that lead to atrial fibrillation. Surgical ablation has a much higher success rate than drug therapies and lacks the potential for side effects presented by drug treatment. However, highly invasive (e.g., open-chest) procedures can present substantial risks.

Catheter ablation techniques use a less invasive approach and create scar tissue via a transvenous approach. A catheter delivers energy or cools tissue to cause lesional scarring without cracking a patient's chest.

While current treatments address atrial fibrillation, further advances in ablation devices and their methods of use would be beneficial.

SUMMARY

Described herein are methods and devices for providing cryoablative therapy. In one aspect, a cryoablative device includes a cryoablation chamber and a volume displacement chamber. In use, the volume displacement chamber can occupy a non-therapeutic volume and reduce the amount of cryofluid required to ablate target tissue.

In one embodiment, a cryotherapy catheter device comprises an elongate catheter shaft extending between a proximal and distal end and an expandable first chamber positioned proximate to the distal end of the catheter shaft. The first chamber can be in fluid communication with a source of cryofluid. An expandable second chamber can be positioned adjacent to the first chamber such that expansion of the second chamber applies pressure on the first chamber. A source of volume displacement fluid can be in fluid communication with the second chamber.

In one embodiment, the first chamber is positioned to deliver cryotherapy when filled with cryofluid. Conversely, the second chamber can be configured to hold the first chamber in contact with tissue when expanded. In one exemplary aspect, the expandable first chamber surrounds at least a portion of the expandable second chamber. In another aspect, the second chamber is completely enclosed by the first chamber. In yet another aspect, the expandable second chamber is positioned at the distal-most end of the catheter, and the expandable first chamber is positioned distally of the second chamber.

In another embodiment, the first and second chambers share a common wall. The wall can be adapted to insulate the volume displacement chamber from the cryofluid chamber. For example, a wall positioned between the first and second chambers can have a lower thermal conductivity than a portion of an outer wall of the first chamber positioned for delivering cryoablative therapy. In another aspect, at least a portion of a wall of the first chamber can have a higher thermal conductivity than a wall of the second chamber.

Further described herein is a cryoablation device having multiple cryoablation chambers. The device can include an elongate catheter shaft extending between a proximal and distal end and an expandable volume displacement chamber positioned proximate to the distal end of the catheter shaft. The volume displacement chamber can be in fluid communication with a source of volume displacement fluid. The device can further include multiple expandable cryochambers located adjacent to the volume displacement chamber and a source of cryofluid in fluid communication with the multiple expandable cryochambers. When expanded, the volume displacement chamber is configured to move at least some of the multiple expandable cryochambers into position for delivering cryoablative therapy.

In another embodiment, a method of delivering croyablative therapy is disclosed. In one aspect, the method includes the steps of providing a catheter device comprising a catheter shaft, an expandable first chamber, and an expandable second chamber. A user positions the catheter device relative to target tissue such that the first expandable chamber is positioned at least partially between the second expandable chamber and target tissue. The first chamber is then expanded by delivering cryofluid into the first expandable chamber and ablating tissue adjacent to the first chamber. In addition, the second expandable chamber is expanded with a volume displacement fluid.

It is to be understood that both the foregoing general description and the following detailed description are exemplary and are not restrictive of the invention, as claimed.

BRIEF DESCRIPTION OF THE DRAWINGS

The accompanying drawings, which are incorporated in and constitute a part of this specification, illustrate exemplary embodiments of the invention and together with the description, serve to explain the principles of the invention.

DETAILED DESCRIPTION

Described herein are methods and devices for ablating tissue, and in particular, for ablating tissue with a cryofluid. In one embodiment, a cryotherapy catheter device is disclosed. The device can include an expandable body comprising first and second expandable chambers that are adapted to receive a cryofluid and a volume displacement fluid, respectively. In one aspect, the first chamber is placed adjacent to target tissue and cryofluid is delivered to effect ablation of the tissue. The second chamber, spaced from the first chamber and target tissue, can be expanded to increase the volume of the expandable body and/or position the first chamber relative to the target tissue for treatment of the target tissue. In one aspect, methods and devices are adapted for cardiac cryoablation, and in yet another aspect, methods and devices are disclosed for reducing the amount of cooling fluid necessary to alter target cardiac tissue and block aberrant electrical signals.

Figure 1:
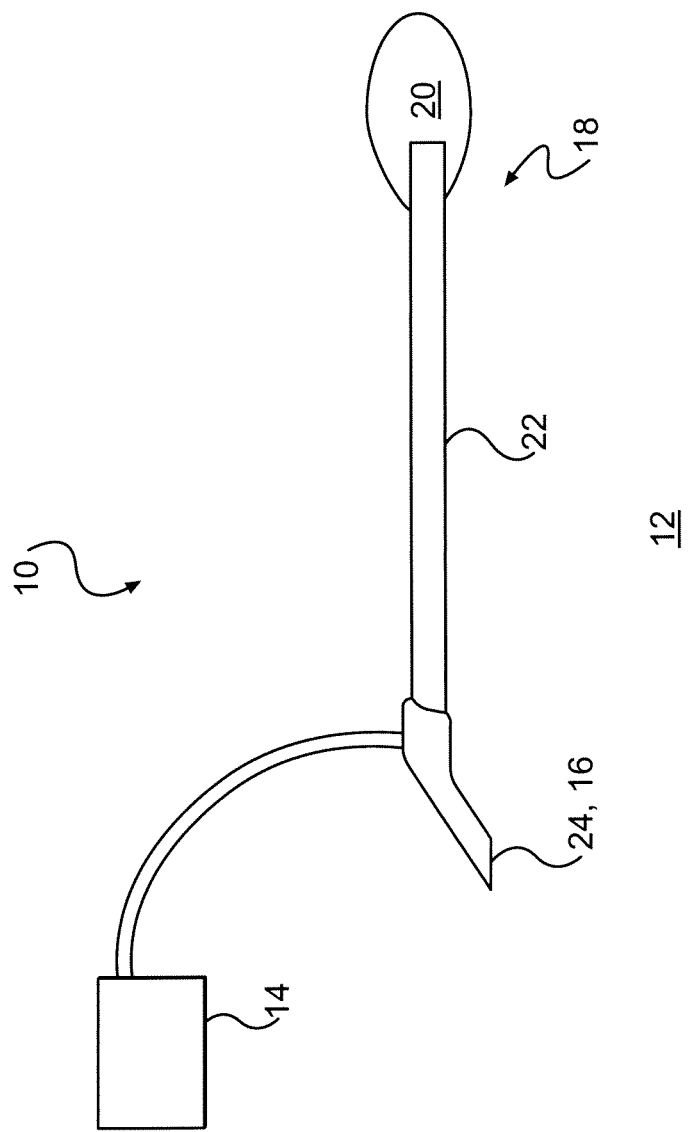
FIG. 1 is a side view of an exemplary embodiment of a cryoablation device described herein.

FIG. 1 illustrates one exemplary embodiment of a system 10 for ablating tissue with cryofluid comprising an ablation device 12 and a source of fluid 14. In one aspect, device 12 includes an elongated body extending between proximal and distal ends 16, 18. The distal end of device 12 can include an expandable body 20 into which cryofluid can be placed as will be discussed in more detail below.

Proximal to expandable body 20, device 12 can include shaft 22. In one aspect, shaft 22 is defined by a flexible or rigid body having one or more channels through which treatment fluids can be delivered. For example, shaft 22 can include at least one lumen for the delivery of a cryofluid and/or at least one lumen for the delivery of a volume displacement fluid. In addition, wires for conducting therapeutic energy and/or for sending/receiving sensed signals can extend along at least a portion of shaft 22. In one aspect, the wires can communicate with sensors positioned at the distal end of shaft 22 and/or on expandable body 20.

The shaft can include a variety of features to facilitate insertion and/or placement of the expandable body relative to target tissue. In one embodiment, device 12 can include an articulating segment defined by a portion of shaft 22. For example, a distal portion of shaft 22 can be actuated by a user from a proximal location to steer expandable body into a target location. In one exemplary aspect, shaft 22 can include push and/or pull strands to transmit forces to the articulation segment.

The size and shape of shaft 22 can be chosen based on the intended use of device 12. Where device 12 is used for cardiac ablation, shaft 22 can be sized and shaped for insertion through a vascular lumen. In addition, the materials and structure of shaft 22 can be chosen to provide a flexible elongated body. One skilled in the art will appreciate that shaft 22 can represent the variety of catheter structures commonly known in the art for a vascular approach. However, the devices described herein need not be delivered via a transvenous route and/or the target tissue need not be cardiac tissue.

The proximal end of device 12 can include a user interface or handle 24 that permits a clinician to grasp device 12. Handle 24 can have a variety of forms depending on the intended use of device 12 and/or the environment in which device 12 is used. In one aspect, handle 24 can include one or more sources of liquid or gas for expanding expandable body 20. Controls for governing the delivery of liquid, such as a cryofluid or volume displacement fluid, can, in one aspect, also be located on handle 24. Alternatively, or additionally, handle 24 can be configured to mate with one or more sources of liquid such as fluid source 14. In one embodiment, source 14 includes a cryofluid and/or volume displacement fluid and can further include a mechanism for regulating and controlling expansion of expandable body 20 via delivery of fluid.

Figure 2:
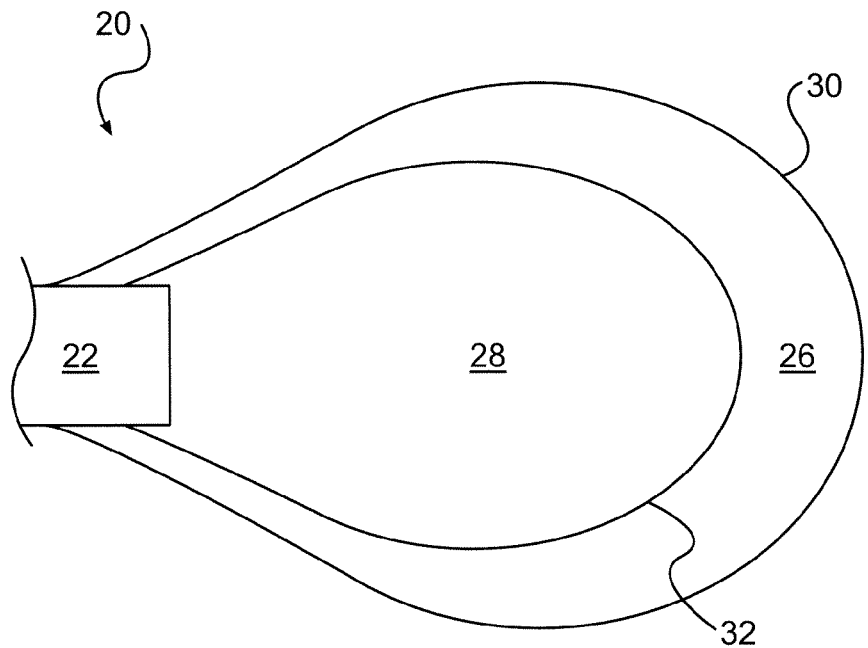
FIG. 2 is a cross-sectional view of one embodiment of a cryoablation device described herein.

Returning to expandable body 20, FIG. 2 is a cross-section of one embodiment of a cryotherapy device in which expandable body 20 is defined by a first and second chamber. First chamber 26 is configured to receive cryofluid and second chamber 28 is adapted to receive a volume expansion fluid. For example, first chamber can be in fluid communication with a cryofluid source. In one aspect, a lumen extends from the proximal end of device 12 to the cryofluid chamber (first chamber 26). The proximal end of the lumen can include a fitting for mating with a source of cryofluid, particularly, with a source of pressurized gas. Conversely, the volume expansion chamber, second chamber 28, can be in fluid communication with a source of volume displacement fluid.

In one aspect, first chamber 26 surrounds at least a portion of the second chamber and/or is positioned adjacent to the exterior or outer surface of second chamber 28. In use, the first chamber is located at least partially between target tissue and the second chamber. The relative location of the first and second chambers allow second chamber 28 to occupy a non-therapeutic volume of the expandable member such that the amount of cryofluid delivered to expandable member 20 is reduced. First chamber 26 can receive cooling fluid and cool target tissue positioned proximate to the first chamber while second chamber 28 can be expanded with a different fluid or higher temperature fluid (e.g., liquid and/or gas).

When positioned within an anatomic structure, such as a vascular structure, expansion of second chamber 28 can assist with positioning and/or shaping first chamber 26. In a first aspect, second chamber 28 may apply pressure against first chamber 26. In this aspect, filling second chamber 28 with volume displacement fluid may act to move first chamber 26 towards or into contact with the target tissue. Additionally, or alternatively it may cause first chamber 26 to adopt a shape that partially conforms to that of the target tissue by pressing chamber 26 into the tissue. In another aspect, second chamber 28 may act as a base from which first chamber 26 may expand. In this aspect, expanded second chamber 28 occupies a non-therapeutic portion of expandable body 20, thus partially defining the shape of first chamber 26 and placing a greater portion of first chamber 26 closer to the target tissue.

Second chamber 28 can also assist with insulating non-target tissue. In this aspect, second chamber 28 may comprise a portion or portions of the outer surface of expandable body 20, thereby excluding first chamber 26 from a portion or portions of the outer surface of expandable body 20. Tissue adjacent to or in contact with first chamber 26 can receive cryotreatment by being located near the cryofluid contained in first chamber 26. The tissue adjacent to or in contact with second chamber 28 can be insulated from the cryofluid contained in first chamber 26 by the fluid displacement fluid contained in second chamber 28, thereby avoiding cryotherapy treatment. Thus by locating second chamber 28 adjacent to or in contact with sensitive tissue, such as tissue not to be treated with cryotherapy or tissue previously treated with cryotherapy, second chamber 28 can protect such sensitive tissue through insulation.

In one embodiment, the first and second chambers are defined by first and second members 30, 32, respectively. The first member 30 defines, at least in part, the boundary of first chamber 26, and second member 32 defines, at least in part, the boundary of the second chamber 28. However, the first and second members need not exclusively define the first and second chambers. For example, as illustrated in FIG. 2, the second member 32 can define the inner surface of the first (outer) chamber and the outer surface of second (inner) chamber 28. The first and second members need not comprise a single contiguous material. For example, the first and second chambers can be defined by one or more walls having the same or different material properties. In addition, the walls of the first and second chambers can include one or more layers.

Regardless, at least a portion of the first and second chambers are expandable. In one aspect, first and second members 30, 32 can be expanded or inflated by stretching. Alternatively, the first and/or second member may be a non-stretchable, but flexible material. A member so constructed could expand by unfolding from an original collapsed and/or folded configuration. In another aspect, at least a portion of the first and/or second member can be deformable. Expansion can be achieved by deforming the walls of expandable member 20.

In one embodiment, outer member 30 and inner member 32 can have different properties. For example, outer member 30 can have a higher thermal conductivity relative to the inner member to facilitate heat transfer between a cryofluid within the first chamber and adjacent target tissue. Conversely, inner member 32 can have a lower thermal conductivity to limit the amount of heat transfer to the cryofluid within the first chamber and/or to inhibit freezing of the volume displacement fluid. A difference in the thermal conductivity can be achieved by using different materials, by using different material thicknesses, and/or by using an insulative layer.

A variety of conventional cooling or cryofluids can be used with the devices described herein. The coolant fluid used to fill the first chamber 26 may be a liquid or a gas, or it may change phase from liquid to gas as it travels from the lumen through the first chamber 26. For example, the coolant may be a liquid with a low freezing point, such as saline, liquid nitrogen or other known heat transfer fluid. Alternatively, the coolant fluid may be a compressed fluid such as nitric oxide or other known refrigerant that expands as it enters the cooling chamber, thus decreasing the temperature of the first chamber 26 through the Joule-Thompson effect. In such instance, both the aerodynamics of the fluid's expansion and the final volume of the first chamber 26 after expansion can affect the final temperature of the coolant fluid.

The fluid used to fill the second chamber 28 can also have a cooling effect and/or can be chosen solely to occupy space and expand the second chamber. In one aspect, the volume displacement fluid is a biocompatible or medical grade fluid such as saline. In addition, the fluid may contain a contrast agent to aid in visualizing the cryotherapy device. In another aspect, the volume displacement fluid is chosen such that the volume displacement fluid does not freeze during cryotherapy treatment. One skilled in the art will appreciate that the volume displacement fluid can be selected depending on a variety of factors including the intended use of device 20, the configuration of the first and second chambers, the chosen cryofluid (e.g., cryofluid temperature), the volume displacement fluid freezing temperature, and/or thermal capacity.

Figure 3:
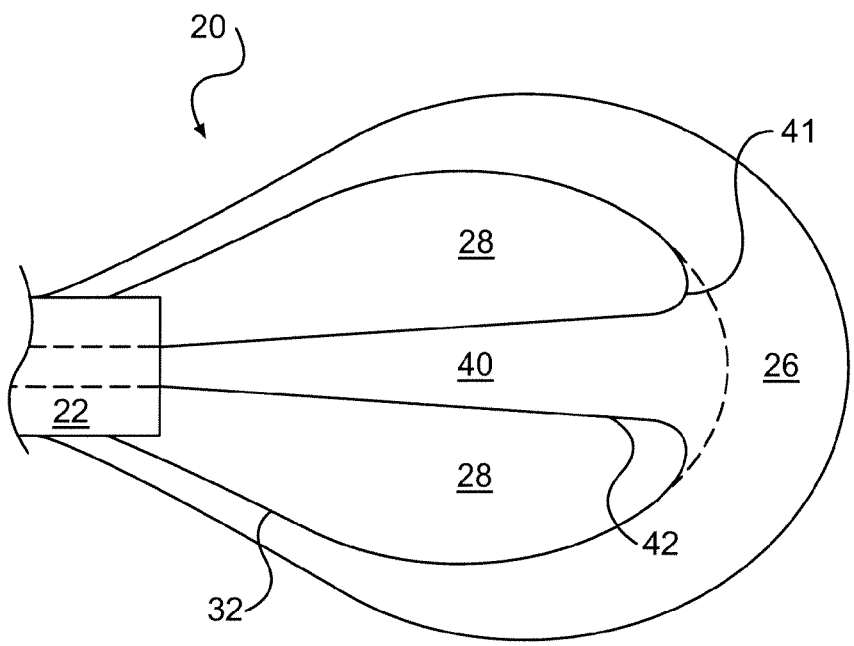
FIG. 3 is a cross-sectional view of another embodiment of a cryoablation device described herein.

In one embodiment, cryofluid travels through the second chamber to reach the first chamber. FIG. 3 is a cross-section of one embodiment of a cryotherapy device having within expandable body 20 first chamber 26, second chamber 28 and a pathway 40 extending through the second chamber 28. In one aspect, the pathway extends from the catheter shaft 22 through second chamber 28 and exits into the first chamber 26.

Pathway 40 can be linear, extending along the longitudinal axis of expandable body 20 and exiting at the distal end of second chamber 28 as shown in FIG. 3. Pathway 40 also may be curvilinear, exiting from second chamber 28 into first chamber 26 at a location spaced from the longitudinal axis of expandable body 20. In another aspect, pathway 40 may be branched, having multiple exit points along inner member 32 into first chamber 26.

In use, routing pathway 40 through second chamber 28 can insulate cryofluid within pathway 40 from sensitive tissue and/or avoid inconsistent or localized cooling. Chamber 28 can space pathway 40 from the outer walls of expandable member 20.

In addition, allowing cooling fluid to enter first chamber 26 at a distance from the proximal end of expandable body 20 can provide more uniform cooling and/or can focus cooling at the distal end of expandable member 20. With respect to FIG. 3, cooling fluid exiting pathway 40 is directed toward first member 30 which direct the cooling fluid along the inner wall of first member 30. As a result, the fluid travels along the wall of the first chamber and mix with fluid within chamber 26. If cryofluid enters chamber 26 immediately adjacent to the proximal end of expandable member 20, the cooling may be concentrated at the proximal end of the expandable member and/or may not mix efficiently. Thus, the size and shape of pathway 40 and the location of its opening into first chamber 26 can be chosen to improve the fluid dynamics and aerodynamics associated with the expansion of the cooling fluid into first chamber 26.

In one aspect, an opening 41 of pathway 40 into chamber 26 is spaced from the proximal end of chamber 26 and/or from the proximal end of expandable member 20. In another aspect, opening 41 is closer to the distal end of chamber 26 and/or expandable member 20 than the proximal end of chamber 26 and/or expandable member 20. In yet another aspect, opening 41 is positioned proximate to a longitudinal axis of expandable member 20.

In one aspect, pathway 40 is defined by a lumen extending through the second chamber and spaced from the sides of expandable body 20. The wall 42 of the pathway can be defined by a portion of the second member 32 and/or a separate structure extending within the second member. In one aspect, wall 42 can have a low thermal conductivity to insulate the cryofluid from second chamber 28.

Figure 4A:
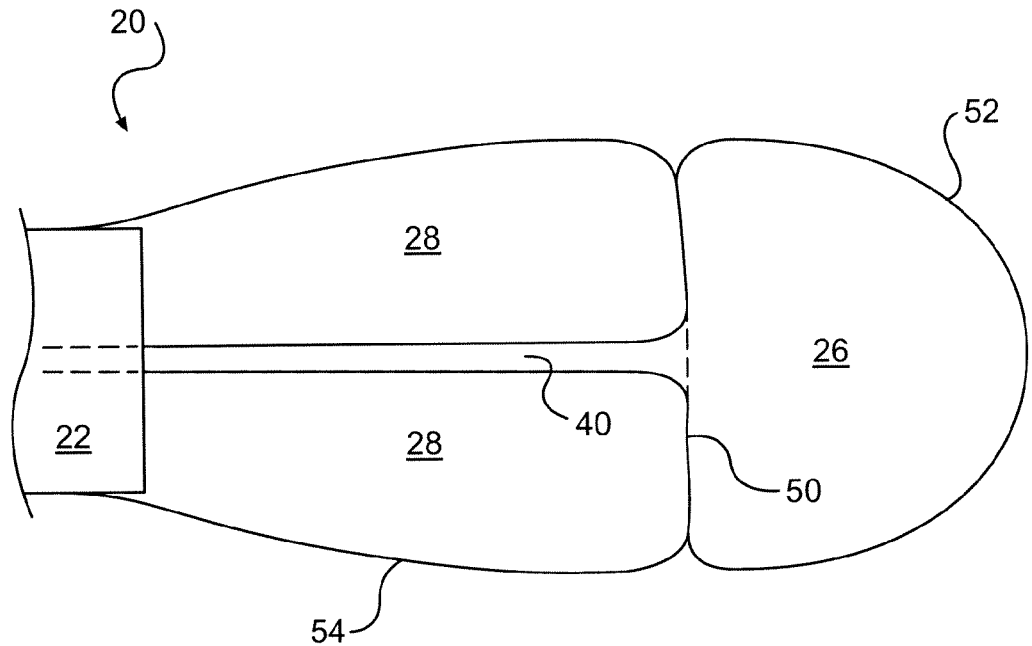
FIG. 4A is a cross-sectional view of yet another embodiment of a cryoablation device described herein.
Figure 4B:
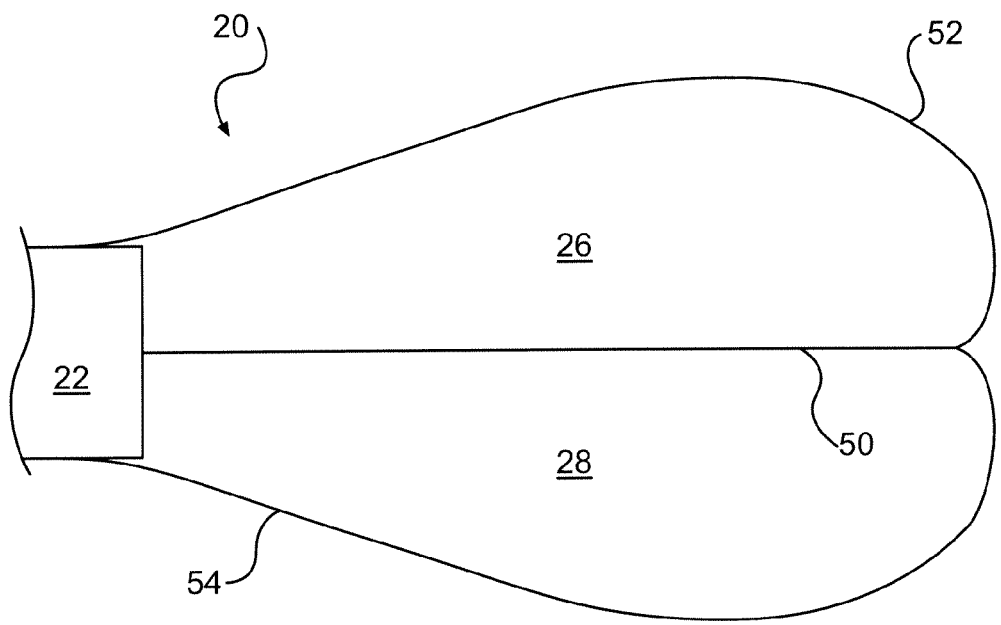
FIG. 4B is a cross-sectional view of still another embodiment of a cryoablation device described herein.

In another embodiment of the invention, a portion of each chamber of expandable body 20 can be positioned adjacent to the outer surface of expandable body 20 and/or partially define the outer surface of expandable body 20. FIGS. 4A and 4B show cross sections of a cryotherapy device having first chamber 26 and second chamber 28 within expandable body 20 where a portion of each chamber partially defines the outer surface of expandable body 20. In this aspect the first and second chambers 26, 28 have a side-by-side configuration rather than an inside/outside configuration as illustrated in FIGS. 2 and 3. In FIG. 4A, the second chamber is located proximate to the distal end of catheter 22, while first chamber 26 is located adjacent to the exterior or outer surface of second chamber 28. In FIG. 4B, the first and second chambers extend parallel to one another.

In one aspect, the first and second chamber are delineated by a wall 50 that extends along a transverse (FIG. 4A) or longitudinal (FIG. 4B) plane. Wall 50 can be positioned along any plane through expandable body 20 which allows the first chamber 26 to be placed in close proximity to tissue to be treated. Further, wall 50 need not be planar. For example, first chamber 26 may curve around a portion of second chamber 28, creating a non-planar wall 50.

In addition to requiring less cooling fluid than a single chamber device, devices like those described in FIGS. 4A and 4B allow for full expansion of expandable body 20 while limiting treatment to only a portion of the tissue on the interior surface of a chosen anatomic region. It may be desirable to treat only the tissue at the distal end of expandable body 20, in which case a device such as the one depicted in FIG. 4B can provide treatment. When it is desired to treat less than the full circumference of tissue surrounding expandable body 20, a device similar to the one shown in FIG. 4B would be useful.

Selective treatment of only a portion of the tissue can be achieved by designing the proper shape of first chamber 26, designing a complimentary shape for second chamber 28, and placing expandable body 20 into the anatomic feature such that first chamber 26 is only adjacent to or in contact with tissue to be treated.

First chamber 26 and second chamber 28 may be the same size or they may each be different in size. Similarly the shape of first chamber 26 may be the same or different than the shape of second chamber 28. Chambers 26 and 28 may have shapes corresponding to the anatomic structure into which expandable body 20 is positioned. For example, chambers 26 and 28 may have a cylindrical, spherical, conical or irregular shape. For example, chambers 26 and 28 may have shapes adapted to expand against the interior walls of the cardiac vasculature. In another aspect, flexible and/or deformable walls of device 12 allow the expandable member to adapted to the surface features of the target anatomic structure.

Figure 5:
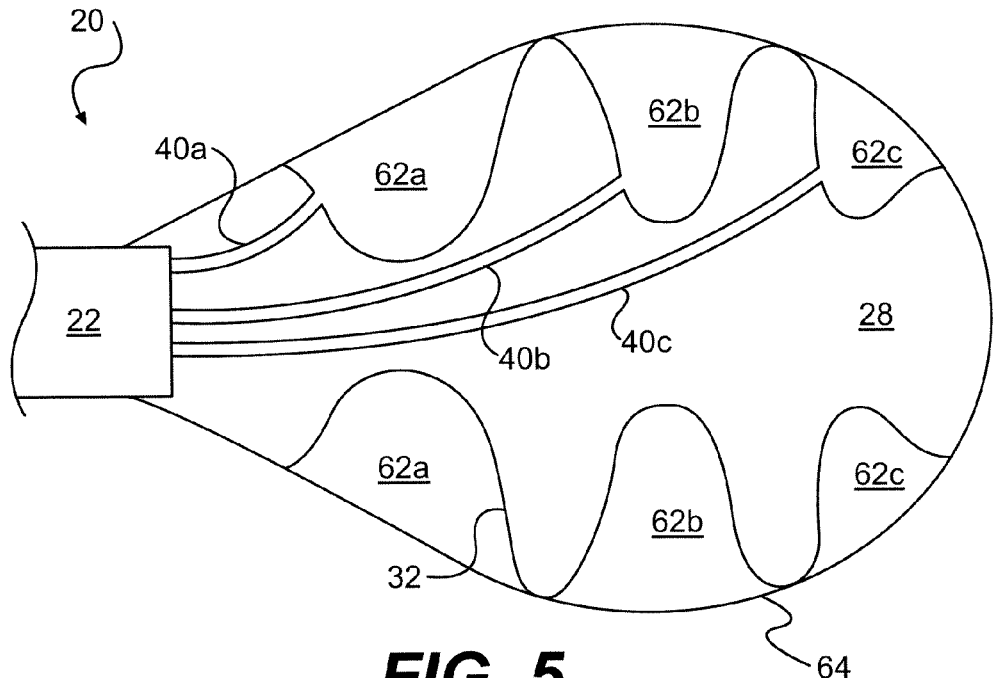
FIG. 5 is a cross-sectional view of another embodiment of a cryoablation device described herein.

FIG. 5 illustrates another embodiment of a cryotherapy device having an expandable volume displacement chamber 28 and multiple cooling chambers 62a-c located within expandable body 20. In one aspect, the multiple cooling chambers 62a-c are positioned adjacent to the exterior or outer surface of the expandable volume displacement chamber 28 and in closer proximity to target tissue. Conversely, second chamber 28 can be located centrally and configured to occupy a non-theraputic volume. In use, the volume displacement chamber (chamber 28) can be expanded to move the cooling chambers into contact with tissue and/or to hold the cooling chambers in contact with tissue.

Such a device allows for the treatment of non-contiguous regions of tissue. For example, the arrangement of multiple cooling chambers 62a-c depicted in FIG. 5 allows for alternating circumferential bands of treated tissue and circumferential bands of untreated tissue. Other patterns of treated and untreated tissue are possible by adapting the location, size and shape of the multiple cooling chambers 62 to form the desired treatment pattern.

In one embodiment, an outer member 64 defines, in part, a boundary of multiple cooling chambers 62 and the outer boundary of expandable body 20. In addition, inner member 32 defines, at least in part, the inner boundary of the multiple cooling chambers 62a-c. In addition, inner member 32 can define the outer boundary of the volume displacement chamber 28. Outer member 64 and inner member 32 can each be expandable.

In another embodiment, each of the individual multiple cooling chambers 62a-c are defined, at least in part, by separate expandable members. In one aspect, inner member 32 may define, in part, the inner boundary of the multiple cooling chambers 62a-c and outer member 64 may be comprised of separate expandable members mated to inner member 32. In this aspect, inner member 32 can also define the outer boundary of the volume displacement chamber 28 and portions of the outer boundary of expandable body 20.

Figure 6:
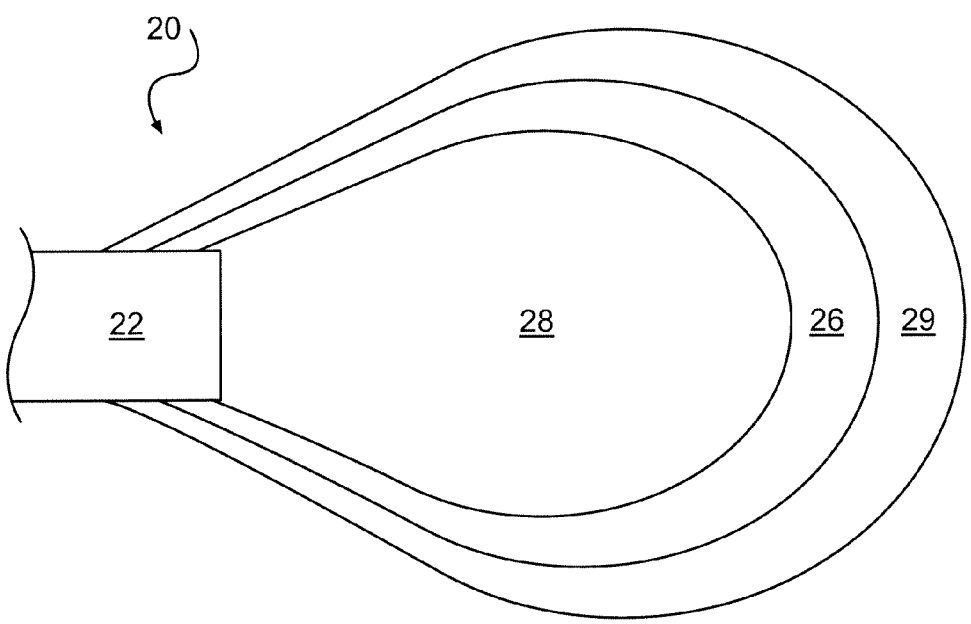
FIG. 6 is a cross-sectional view of another embodiment of the device of FIG. 2.

Further described is an expandable body 20 with a protective outer layer. In any of the embodiments described herein, an additional expandable body can surround the first and/or second chambers. In one aspect, the outer layer can space the cryoablation chamber from target tissue to control or limit the amount of heat removed and/or the depth of ablation. For example, FIG. 6 illustrates outermost chamber 29 positioned in a surrounding relationship to first and second chambers 26, 28. The outermost chamber can receive a source of volume displacement fluid that occupies an area between a surface of the first chamber 26 and target tissue. In addition, or alternatively, the walls of chamber 29 can provide an additional layer of protection should one of the chambers rupture or break.

In one aspect, device 12 can incorporate or communicate with systems or devices for cardiac mapping. For example, expandable body 20 can incorporate sensors for sensing cardiac signals in adjacent tissue. Such sensors can be positioned on the outer surface of the expandable body and/or within (or inside) an outer layer of device 12 that permits sensing therethrough.

Further described herein are methods of delivering cryoablative therapy. In one embodiment, expandable body 20 can be positioned adjacent to target tissue such as, for example, cardiac tissue. Once in position, the first and second chambers can be filled (or partially filled, or further filled) to position the cooling chamber in position for delivery cryoablative therapy. In one aspect, cryofluid is delivered to the first chamber. For example, cryofluid can flow from a fluid source through catheter 22 and into the first chamber. A user or controller can regulate the delivery of cryofluid and/or volume displacement fluid to achieve the desired expansion. Alternatively, the expandable body 20 can be constrained to limit the maximum expansion of the first and/or second chambers.

In one aspect, the expandable body 20 can be partially expanded by filling the second chamber 28 with fluid. Expandable body 20 can then be further expanded by filling the first chamber 26 with cooling fluid. In one aspect, first chamber 26 is expanded until expandable body 20 is in intimate contact with tissue to be treated. Expandable body 20 may remain in this expanded state for the time period required to ablate the tissue adjacent to the first chamber 26. Following this treatment period, cooling fluid can be removed from first chamber 26, and volume displacement fluid can be removed from second chamber 28.

Alternatively, after placement of expandable body 20 near the tissue to be treated, expandable body 20 can be partially expanded by first filling the first chamber 26 with cooling fluid. After filling the first chamber 26 with the desired amount of cooling fluid, expandable body 20 can be expanded in order to place the first chamber 26 adjacent to the tissue to be treated by filling the second chamber 28 with fluid. Expandable body 20 can remain in this expanded state for the time period required to ablate the tissue adjacent to the first chamber 26. Following the treatment period, cooling fluid can be removed from first chamber 26 and volume displacement fluid can be removed from second chamber 28.

A third method of using system 10 involves locating expandable body 20 near the tissue to be treated and first expanding expandable body 20 by filling the second chamber 28 with fluid until the second chamber 28 is adjacent to the tissue to be treated. At this point second chamber 28 accounts for most of the volume of expandable body 20. Next, cooling fluid is added to the first chamber 26 while at the same time fluid is removed from the second chamber 28 such that the overall volume of expandable body 20 remains substantially unchanged. This allows the first chamber 26 to expand into the region adjacent to the tissue to be treated and causes the second chamber 28 to be partially displaced away from the tissue to be treated. Following the treatment period the cooling fluid can be removed from the first chamber 26 and the fluid can be removed from the second chamber 28.

Other embodiments will be apparent to those skilled in the art from consideration of the specification and the disclosure therein. It is intended that the specification and examples be considered as exemplary only, with a true scope and spirit of the invention being indicated by the following claims.

What is claimed is:

1. A cryotherapy catheter device comprising:
    an elongate catheter shaft extending along a longitudinal axis between a proximal and distal end;
    an expandable first chamber positioned proximate to the distal end of the catheter shaft, the first chamber in fluid communication with a lumen for transmitting cryofluid to the first chamber;
    a source of cryofluid that is in fluid communication with the first chamber;
    an expandable second chamber positioned proximate to the first chamber;
    a source of volume displacement fluid in fluid communication with the second chamber,
    wherein the first chamber is positioned transversely with respect to the second chamber, wherein the first and second chambers share a common wall that insulates the second chamber from the first chamber, the common wall limiting heat transfer between the first and second chambers, and wherein the second chamber is positioned to occupy a non-therapeutic volume when expanded.

2. The device of claim 1, wherein, when expanded, the second chamber and the volume displacement fluid are configured to insulate tissue from the first expandable chamber and the cryofluid.

3. The device of claim 1, wherein at least a portion of the second chamber extends longitudinally from the catheter shaft.

4. A cryotherapy catheter device comprising:
    an elongate catheter shaft extending along a longitudinal axis between a proximal and distal end;
    an expandable first chamber positioned proximate to the distal end of the catheter shaft, the first chamber in fluid communication with a lumen for transmitting cryofluid to the first chamber;
    a source of cryofluid that is in fluid communication with the first chamber;
    an expandable second chamber positioned proximate to the first chamber;
    a source of volume displacement fluid in fluid communication with the second chamber,
    wherein in the first chamber is positioned longitudinally with respect to the second chamber, wherein a common wall positioned between the first and second chambers insulates the volume displacement fluid from the cryofluid when the first and second chambers are expanded, the common wall limiting heat transfer between the first and second chambers, and wherein the second chamber is positioned to occupy a non-therapeutic volume when expanded.

5. The device of claim 4, wherein the first chamber is positioned distally with respect to the second chamber.

6. The device of claim 4, wherein a distal wall of the first chamber has a higher thermal conductivity than the wall.

7. A cryotherapy catheter device comprising:
    an elongate catheter shaft extending between a proximal and distal end;
    an expandable body, the expandable body comprising:
        an expandable volume displacement chamber positioned proximate to the distal end of the catheter shaft, the chamber in fluid communication with a source of volume displacement fluid; and
        multiple expandable cryochambers located adjacent to the volume displacement chamber; and
    a source of cryofluid in fluid communication with the multiple expandable cryochambers,
    wherein the volume displacement chamber is configured to move at least some of the multiple expandable cryochambers into position for delivering croablative therapy when expanded, wherein an outer member defines, at least in part, an outer boundary of the multiple expandable cryochambers and an outer boundary of the expandable body, and an inner member defines, at least in part, an inner boundary of the multiple expandable cryochambers and an outer boundary of the volume displacement chamber.

8. The device of claim 7, where at least two of the multiple expandable cryochambers are separated from one another by the expandable volume displacement chamber when the volume displacement chamber is expanded.

9. The device of claim 7, where each expandable cryochamber circumscribes the expandable volume displacement chamber.

* * * * *